United States Patent [19]

Ritter et al.

[11] Patent Number: 5,051,363
[45] Date of Patent: Sep. 24, 1991

[54] METHOD FOR MODIFYING THE TOXICITY OF DNA REACTIVE CROSS-LINKING AGENTS TO CELLS

[75] Inventors: Carl Ritter, Clifton Heights; Robert J. Rutman, Philadelphia, both of Pa.

[73] Assignee: University of Pennsylvania, Philadelphia, Pa.

[21] Appl. No.: 67,190

[22] Filed: Jun. 26, 1987

[51] Int. Cl.$^5$ ............................................. C12N 5/00
[52] U.S. Cl. ................................ 435/240.3; 435/240.1
[58] Field of Search .................... 435/6, 240.3, 240.1; 436/91, 88; 514/1, 44; 530/380; 536/27

[56] References Cited

PUBLICATIONS

Kwon et al., Cancer Res. 47: 1505–1508 (1987).
Woolley et al., Cancer Res. 41: 3890–3900 (1981).
Rutman, R. J. et al., "Experimental Chemotherapy Studies II. The Reactions of Chloroquine Mustard (CQM) and Nitrogen Mustard (NH2) with Ehrlich Cells", *Cancer Res.*, 21: 1134–1140, 1961.
Chun, E. H. L. et al., "Differences in the In Vivo Alkylation and Cross-Linking of Nitrogen Mustard-Sensitive and -Resistant Lines of Lettre-Ehrlich Ascites Tumors", *Cancer Res.*, 29:1184–1194, 1969.
Lyons, R. M. et al., "Active Transport of Nitrogen Mustard and Choline by Normal and Leukemic Human Lymphoid Cells", *Cancer Res.*, 32:1679–1685, 1972.
Rutman, R. J. et al., "Observations on the Mechanism of the Alkylation Reaction Between Nitrogen Mustard and DNA", *Biochim. Biophys. Acta*, 174:663–673, 1969.
Ritter, C. et al., "Modulation of the Cellular Toxicity of Nitrogen Mustard in Murine Cells", *Cancer Res.*, 47:472–476, Jan. 15, 1987.
Ritter, C. et al., "Phospholipid Stereospecificity in Liposomal Modulation of Nitrogen Mustard Action", presented on Jun. 26, 1987, Conference of the NATO Advanced Study Institute, Targeting of Drugs: Anatomical and Physiological Considerations, Greece.
Sandvig K. and Olsnes S., "Entry of the Toxic Proteins Abrin, Modeccin, Ricin, and Diphtheria Toxin into Cells, I. Requirement for Calcium", *J. Bio. Chem.*, vol. 257, No. 13, pp. 7495–7503 (1982).
Sandvig K. and Olsnes S., "Entry of the Toxic Proteins Abrin, Modeccin, Ricin, and Diphtheria Toxin into Cells, II. Effect of pH, Metabolic Inhibitors, and Ionophores and Evidence for Toxin Penetration from Endocytotic Vesicles", *J. Bio. Chem.*, vol. 257, No. 13, pp. 7504–7513 (1982).

*Primary Examiner*—Elizabeth C. Weimar
*Assistant Examiner*—Jasemine C. Chambers
*Attorney, Agent, or Firm*—Woodcock Washburn Kurtz Mackiewicz & Norris

[57] ABSTRACT

The cytotoxicity of DNA reactive cross-linking agents can be modified or reversed by exposing cells exposed to such agents to specific endocytotically absorbed materials. These materials should be capable of interfering with the cross-linking of the DNA. For example, electrophillic materials such as serum proteins, are useful for this purpose.

6 Claims, No Drawings

METHOD FOR MODIFYING THE TOXICITY OF DNA REACTIVE CROSS-LINKING AGENTS TO CELLS

BACKGROUND OF THE INVENTION

This invention relates to a method for modifying the toxicity of DNA reactive cross-linking agents such as nitrogen mustard. More particularly, the invention relates to treating cells exposed to DNA reactive cross-linking agents with one or more endocytotically transported electrophyllic or chemically reactive materials such as serum albumin to decrease the toxicity of the drug to the exposed cells.

Advances in the treatment of tumors have come quickly in the last several decades. One common method of treating cancer patients is through "chemotherapy", therapy in which the cancer patient is treated with certain drugs capable of killing cancer cells. A class of drugs useful for chemotherapy are nucleophillic materials capable of being absorbed into the nucleus of a cell endocytotically and there cross-linking the DNA, referred to hereinafter as DNA cross-linking agents. These cross-linking agents are bifunctional compounds, possessing at least two nucleophillic centers capable of covalently bonding to electrophyllic centers in the DNA macromolecule. Cross-linking the DNA in the cell serves to kill the cell as it no longer has normal nuclear functions.

Nitrogen mustards (such as nitrogen mustard itself, methyl-N-bis-(2-chloroethyl)-N-ethylamine, commonly referred to as HN2 or mustargen) are DNA cross-linking agents and were the first chemotherapeutic agents applied to the treatment of tumors. It has been reported that HN2 taken up by the cell travels through the cytoplasm to the nucleus and bifunctionally alkylates DNA. Rutman, R. J., Steele, W. J., Price, C. C., "Experimental Chemnotherapy Studies II. The Reactions of Chloroquine mustard (CQM) and Nitrogen Mustard (HN2) With Ehrlich Cells," *Cancer Res.*, 21:1134–1140, 1961. The cytostatic effect of HN2 is known to be proportional to the degree to which DNA in the cell is cross-linked. Chun and Rutman, et al., *Cancer Research*, (1966); Lyons, R. M. and Goldenberg, G. J., "Active Transport of Nitrogen Mustard and Choline by Normal and Leukemic Lymphoid Cells," *Cancer Res.* 32, 1679–1685, 1972. It has been reported that the alkylation and cross-linking of DNA by HN2 proceeds as two pseudo-first-order reactions; at 37° no unstable displaceable intermediates are observed, but the cross-linking reaction can be interrupted by nucleophillic competition. Rutman, R. J., Chun, E. H. L. and Jones, J., "Observations on the Mechanism of the Alkylation Reaction Between Nitrogen Mustard and DNA," *Biochim. Biophys. Acta.* 174:663–673 (1969).

A well known problem inherent in the use of chemotherapeutic agents such as nitrogen mustard, however, is the fact that the chemotherapeutic agents are relatively nonselective. They are toxic not only to the target cancer cells but also to normal, non-cancerous cells such as those in bone marrow and other rapidly dividing tissues and organs, a fact which can severely limit the clinical use of the agents. Sensitive patients receiving such drugs may require a substantial reduction in dose, to less effective levels, because of toxic side effects such as extreme depression of white blood cell count. With repeated courses of treatment, there is a threat of cumulative injury to the nontarget cells. There is therefore a clear need for a method which would allow one to utilize effective chemotherapeutic agents in the treatment of tumors without causing serious side effects to the patient.

It is an object of this invention to provide a method for modifying the cytotoxic effects of DNA reactive cross-linking agents such as nitrogen mustard. It is a further object of this invention to provide a method by which DNA reactive cross-linking chemotherapeutic agents can be used effectively to treat tumors while significantly reducing the toxic side effects to non-target cells. These and other objects will be clear from the following description of this invention.

SUMMARY OF THE INVENTION

It has now been found that the cytotoxicity of DNA reactive cross-linking agents can be modified or reversed by exposing cells exposed to such agents to specific endocytotically absorbed materials capable of interfering with the cross-linking of the DNA. Very specifically, it has been found that the cytotoxic efficacy of nitrogen mustard and the level of nuclear damage can be reduced by exposing treated cells to serum protein.

DETAILED DESCRIPTION OF THE INVENTION

The DNA reactive cross-linking chemotherapeutic agents referred to in this application are agents well known in the art. These agents are bifunctional electrophillic or reactive compounds capable of tightly binding to the DNA macromolecule. Included in this class, besides the nitrogen mustard, are other nitrogen mustards such as galactose mustard, L-phenylalanine mustard and cyclophosphoamide mustard, as well as compounds such as formamide, doxorubicin, amphotericin B, mitomycin, 1,3-bis(2-chloroethyl)-1-nitrosourea (carmustine), thio TEPA, dimethyl myleran, trimethyldamine, and numerous others.

The materials which, according to this invention, are capable of inhibiting the cytotoxic effects of certain chemotherapeutic agents are materials which are capable of being absorbed into the cell through endocytosis and which are capable of interfering with the cross-linking of DNA. Endocytosis, of course, is an active process in which extracellular materials are introduced into the cytoplasm of cells as the contents of small membrane-bound vesicles. It is believed, although the inventors do not intend to be bound by this theory, that the electrophilic sites on certain endocytotically absorbed materials compete with electrophilic sites on the DNA for the functional groups of the chemotherapeutic agent, thus reducing the frequency of DNA cross-linking to itself. Examples of such electrophillic agents which inhibit HN2 cytotoxicity and DNA cross-linking include serum proteins, in particular albumin, lipoproteins, neuropeptides and hormones. Other materials which are believed to interfere with the cross-linking of DNA are mytotic inhibitors and regulatory ions, e.g., vincristine and $Ca^{++}$. See Ritter, C., Rutman, R. J. and Goldstein, N. O., "Modulation of the Cellular Toxicity of Nitrogen Mustard in Murine Cells," *Cancer Research*, Jan. 15, 1987, the disclosure of which is hereby incorporated by reference.

The method of this invention has been proven in in vitro tests utilizing Lettre-Ehrlich tumor cells, nitrogen mustard and serum albumin. The unique feature of the method is that the cytotoxicity of nitrogen mustard has been reduced even after the nitrogen mustard is absorbed in the cell and is in the process of cross-linking the DNA. It is anticipated that the method of this invention could be applied to the actual treatment of tumors by treatment of chemotherapy patients with the protective agents described herein following drug treatment, or by occluded regional perfusion with drug and simultaneous or subsequent systemic perfusion with protective agent.

Depending on the DNA-reactive crosslinking agent, post-treatment with protective agents can be immediate or delayed, but must precede completion of the second step of the in vivo reactions which are responsible for cross-linking. In the case of HN2, this time frame is about one to five minutes. In the case of alkeran, this time frame could be up to six hours, and in the case of cytoxan, the time frame is between about two to six hours.

Since electrophillic materials endocytotically absorbed function to decrease the cytotoxicity of DNA reactive cross-linking agents, it follows that a treatment which might depress endocytosis of electrophillic materials normally present in a patient's bloodstream would operate to enhance the cytotoxicity of the DNA reactive cross-linking agent. This treatment would be expected to reduce the presence of electrophillic materials in the nucleus which compete with the chemotherapeutic drug for nucleophillic sites on the DNA. Thus, a further method of this invention relates to a method of enhancing the toxicity of DNA-reactive cross-linking agents to cells comprising exposing such cells to an effective toxic amount of said DNA-reactive cross-linking agent followed by exposing such cell to an effective amount of one or more agents which depress endocytosis. Treatment with the endocytosis-depressing agents should preferably follow treatment with the DNA-reactive cross-linking agent as simultaneous treatment might adversely affect transport of the DNA-reactive cross-linking agent in the cell. The timing for such post-treatment would depend on the particular DNA-reactive cross-linking agent used and the length of time necessary for such agent, when applied, to be transported to cell nuclei.

For each electrophillic protective agent or endocytosis-depressing agent, a dose-dependency scale is formulated. Electrophillic materials are effective at or near their physiological concentration (2–5%) as described in the claimed method.

Experimental

Lettre-Ehrlich cells, grown in the peritoneal cavities of female HA/ICR mice for four days were washed free of erythrocytes using phosphate buffered saline ("PBS", 154 mM NaCl, 6.2 mM KCl, 1.5 mM $NaH_2PO_4$, 9.4 mM $Na_2HPO_4$) pH 7.4, and counted. Cells were treated in vitro either with HN2 alone or with HN2 in combination with Ca and/or liposomes. Incubation of cells was done at 37 degrees C. in 15 ml. centrifuge tubes each of which contained 5 ml of PBS. Each incubation was done in duplicate to measure uptake and cytotoxicity simultaneously. When either Ca or liposomes were used, they were added first, then five minutes later, $1 \times 10^7$ living cells were added. Five minutes after that, 24 μM HN2 was added and the incubation continued for five minutes. HN2 uptake was stopped by adding 6 ml ice cold PBS to each tube and placing it in an ice bath. The living and dead cells were washed four times in ice cold PBS to remove extracellular HN2. Then, three sets of duplicate tubes containing cells which had been incubated with HN2 plus liposomes plus Ca were postincubated at 37 degrees C. in 5 ml of either PBS or 2% albumin in PBS or in ascites fluid freed of cells. These postincubations were terminated as before and the cells were washed two times with ice cold PBS.

The cells which had been incubated with tracers were analyzed by scintillation counting. The results were compared statistically by student's t-test, with $p = <0.05$ considered significant. As can be seen from the results presented below in Table 1, postincubation in 2% bovine serum albumin or ascitic fluid which contained 1.8% protein did not significantly decrease HN2 content of cells compared to postincubation in PBS, i.e., the amount of drug which remained bound was very similar whether the postincubation medium contained albumin or not.

TABLE 1

| Treatment | Post-incubation | HN2 Units/Protein |
|---|---|---|
| HN2 | — | 1567 |
| HN2 + αDPC Liposomes + Ca++ | — | 2018 |
| HN2 + αDPC Liposomes + Ca++ | PBS | 1199 |
| HN2 + αDPC Liposomes + Ca++ | Albumin | 1274 |
| HN2 + αDPC Liposomes + Ca++ | Ascitic Fluid | 1119 |

The cells which had been incubated in HN2 were inoculated into a group of eight recipient HA/ICR female mice (0.1 ml/mouse); $10^6$ cells/mouse). Mouse survival was followed for seventy days. The differences in survival produced by the various treatments were compared statistically with a Wilcoxon rank test, with $p < 0.05$ considered significant. Results are presented in Table 2.

TABLE 2

| Postincubation Treatment | % Survival of Treated Mice after X Days |||||||||||
|---|---|---|---|---|---|---|---|---|---|---|---|
| | No. of Days After Incubation |||||||||||
| | 15 | 18 | 20 | 21 | 22 | 23 | 25 | 27 | 40 | 60 | 70 |
| I. In PBS | 100 | 100 | 100 | 100 | 100 | 100 | 100 | 87 | 87 | 87 | 75 |
| II. Albumin/Ascitic Fluid* | 100 | 94 | 63 | 37 | 25 | 19 | 19 | 19 | 19 | 19 | 19 |
| III. No Treatment | 100 | 100 | 100 | 87 | 87 | 87 | 75 | 75 | 75 | 75 | 75 |

| Postincubation Treatment | Relative HN2 Initially** Present in Cells |
|---|---|
| I. | 0.59 |
| II. | 0.63 |

TABLE 2-continued

| | |
|---|---|
| III. | 1.00 |

Results for postincubation in 2% bovine serum albumin in PBS and in mouse ascitic fluid were not significantly different and were combined.
**Relative to HN2 + αDPC liposomes + Ca$^{++}$

Discussion of Results

The data in Table 1 show that when cells were treated with Ca or Ca plus liposomes in the presence of HN2, their HN2 content was increased about 25% above that in cells treated with HN2 alone, in agreement with past results. Ritter et al., supra. Cells which are treated in this way contain two intracellular fractions: bound and free. That which is free flows from the cells when postincubated at 37° C. in drug-free PBS. Ritter et al., supra. Thus, cells postincubated in PBS, in this experiment, lost about 40% of their HN2 as did cells postincubated in either bovine or mouse albumin. The amount of drug which remained bound was very similar whether the postincubation medium contained albumin or not.

The therapeutic efficacy of each of the treatments was measured by injecting treated cells into recipient mice and following mouse survival. As shown in Table 2, most of the cells treated with HN2 or with HN2 plus liposomes plus Ca then PBS washed were killed, indicated by 75% mouse survival. These results are also similar to those previous reported for such treatment. Ritter et al., supra.

When Lettre-Erhlich cells are incubated at 37° C. in PBS containing 24 μM HN2 for five minutes, sufficient drug is accumulated, in the nuclei, to kill over 99.9% of the cells. Ritter et al., supra. After receiving PBS-postincubated cells which had lost their unbound intracellular HN2, two of the recipient eight mice died, one 27 days later and one 68 days later. Based on cell titration of mouse survival, estimates can be made as to the number of viable cells which were injected (Rutman, R. J., Steele, W. J. et al., supra.), and thus the mouse which died between 26 and 27 days received approximately $10^4$ to $10^5$ viable cells and the mouse which died between 68 and 69 days received between one and ten viable cells. There were no viable cells in the six mice which survived. Since a total of $8 \times 10^6$ were injected and $1 \times 10^5$ cells remained viable, the fraction cell survival was 1.25%. The albumin-postincubated cells were injected into sixteen mice, 13 of which died with a mean survival time of 18 days, indicating that in each of those mice between 1 and $8 \times 10^6$ cells remained viable, the fractional survival was approximately 100%. Albumin treatment essentially nullified the cytotoxic effect of the intracellularly bound drug. Since, as previously mentioned, the cytotoxic effect of HN2 is known to be proportional to the degree to which DNA is cross-linked, it is possible that nuclear HN2 has been bound by a reaction with a target during the initial five minute 37° C. incubation. While postincubation at 37° C. in PBS permits formation and/or completion of the lethal crosslinks, apparently postincubation in albumin either does not or discharges the effective state before cytotoxic results set in.

What is claimed is:

1. A method of decreasing the toxicity of nitrogen mustard to cells exposed to nitrogen mustard comprising exposing said cells to an effective amount of one or more materials selected from mitotic inhibitors, regulatory ions, and serum proteins, said material being capable of interfering with cross-linking of DNA.

2. A method of claim 1 where said cells are first exposed to a cytotoxic amount of said nitrogen mustard and prior to completion of the cytotoxic reaction such as cross-linking, said cells are exposed to an effective amount of said material selected from mitotic inhibitors, regulatory ions, and serum proteins, said material being capable of interfering with the cross-linking of DNA.

3. The method of claim 1 wherein said mitotic inhibitor is vincristine.

4. The method of claim 1 wherein said regulatory ion is calcium.

5. The method of claim 1 wherein said serum protein is albumin.

6. The method of claim 1 wherein said nitrogen mustard is N-bis-(2-chloroethyl)-N-ethylamine.

* * * * *